(12) United States Patent
Lee et al.

(10) Patent No.: US 8,529,512 B2
(45) Date of Patent: Sep. 10, 2013

(54) CYLINDER PUMP

(75) Inventors: Sang Bin Lee, Seoul (KR); Kun-Hyung Lee, Seoul (KR); Jeong Ju Lee, Seoul (KR); Jae Soon Choi, Gyeonggi-do (KR); Seung Won Lee, Gyeonggi-do (KR)

(73) Assignee: Meinntech Co., Ltd., Gyeonggi-Do (KR)

( * ) Notice: Subject to any disclaimer, the term of this patent is extended or adjusted under 35 U.S.C. 154(b) by 0 days.

(21) Appl. No.: 13/543,294

(22) Filed: Jul. 6, 2012

(65) Prior Publication Data

US 2013/0006183 A1   Jan. 3, 2013

Related U.S. Application Data

(63) Continuation of application No. PCT/KR2010/002152, filed on Apr. 8, 2010.

(30) Foreign Application Priority Data

Jan. 6, 2010 (KR) .................. 10-2010-0000924

(51) Int. Cl.
*A61M 1/00* (2006.01)
(52) U.S. Cl.
USPC ............................................ 604/152
(58) Field of Classification Search
USPC ............................................. 604/151, 152
See application file for complete search history.

(56) References Cited

U.S. PATENT DOCUMENTS

| 4,705,464 A | 11/1987 | Arimond |
| 8,029,480 B2 * | 10/2011 | Lee ............................. 604/246 |
| 8,251,679 B2 * | 8/2012 | Kuehner et al. ............ 417/413.1 |

FOREIGN PATENT DOCUMENTS

KR        10-0127834 B1    4/1998
KR    10-2008-0085911 A    9/2008

OTHER PUBLICATIONS

International Search Report dated Nov. 3, 2010 in connection with corresponding PCT/KR2010/002152.

* cited by examiner

*Primary Examiner* — Aarti B Berdichevsky
(74) *Attorney, Agent, or Firm* — Kramer & Amado P.C.

(57) ABSTRACT

The present invention relates to a simple and small cylinder pump, which can stably supply a medical fluid regardless of the installed height of a liquid container or a blood bag. The cylinder pump includes an upper casing, and a lower casing coupled to the upper casing. An upper rotation member is rotatably inserted in the upper casing. A lower rotation member slidingly contacting the upper rotation member is rotatably inserted in the lower casing. An inner wall of the upper casing, a lower outer surface of the upper rotation member, an inner wall of the lower casing, and an upper outer surface of the rotation member constitute a cylinder having a single-tube shape. Plungers are installed on the upper rotation member and on the lower rotation member, respectively, and rotate in the cylinder, the ends of which are closed.

12 Claims, 13 Drawing Sheets a)

b)

c)

d)

e)

f)

g)

h)

CYLINDER PUMP

This application is a continuation of and claims priority to PCT Application No. PCT/KR2010/002152 filed on Apr. 8, 2010, and claims priority to Korean Patent Application No. 10-2010-0000924 filed Jan. 6, 2010. The entire disclosures of the PCT Application No. PCT/KR2010/002152 published as WO 2011/083892, and KR Application No. 10-2010-0000924 are hereby incorporated by reference in their entirety.

FIELD

The present invention relates to a cylinder pump, and more specifically to a cylinder pump which is simple in structure and small in size, and allows the possibility of remote control regardless of the installation height of the receptacle or blood pack and the possibility of stable injection of a liquid medication or blood.

BACKGROUND

It uses a syringe pump or infusion pump in order to inject a liquid medication or blood (hereinafter, 'liquid medication or blood' will be briefly described 'liquid medication') into the patient while controlling it at a constant and considerably high degree of precision.

The conventional infusion pump has a high failure rate because overload is applied to the machine due to differences in elasticity of the tube by manufacturers. To get a high degree of precision for a syringe pump, the machine becomes complicated with a large size, and its use is possible only if it is installed immovably at a position. Although the syringe pump has a high degree of precision, it is hard to use it as a large volumetric pump, and using it as a large volumetric pump has an inconvenience that it has to be operated repetitively.

In addition, the conventional syringe pump or infusion pump has the pressure of the discharged a liquid medication varied according to the installation position of the receptacle or blood pack, namely, the head of liquid. Therefore, there is inconvenience in that the receptacle or blood pack has to be installed at a certain height by using a pole.

Also, since the degree of precision of the syringe pump or infusion pump is limited beforehand, a pump requiring a high degree of precision has the low feed rate of a liquid medication. Therefore, there is no way to use a syringe pump or infusion pump having different capacity according to the required injection rate and degree of precision of the liquid medication, so it becomes a burden to user that many syringe pumps or infusion pumps need to be provided beforehand.

Moreover, the conventional infusion pump is of a type pressed or squeezed tube by the terminal of the machine, and the syringe pump is of a type that medicine is injected by pushing the plunger of syringe. Therefore, these pumps are all of a type of controlling medicine indirectly, so they may have the terminal overloaded or the machine structure is complicated; reliability is low because of frequent troubles, the price is high, nursing manpower is required, and remote control is difficult.

SUMMARY

Accordingly, to solve the above problems, it is an object of the present invention to provide a cylinder pump which is simple in structure and small in size, allows for the possibility of stable injection of a liquid medication regardless of the installation height of the receptacle or blood pack, prevents overload of the machine, reduces required manpower by dint of remote control, and can use less accessory tubes, etc. that cause environmental pollution and are harmful to the human body.

In order to accomplish the foregoing object, there is provided a cylinder pump comprising a cylindrical upper casing inside which an upper rotator is rotatably inserted; and a cylindrical lower casing which is engaged with the upper casing and inside which a lower rotator that is in rotation sliding contact with the upper rotator is rotatably inserted, the cylinder pump characterized in that: The inner wall of the upper casing and the lower outer circumference of the upper rotator, and the inner wall of the lower casing and the upper outer circumference of the rotator form a single tubular cylinder, the upper rotator and the lower rotator include plungers mounted thereon respectively, which make rotation in the tubular cylinder of whose ends are closed, the cylinder is provided with an inlet tube for a liquid medication to be flowed in and an outlet tube for the liquid medication to be flowed out, wherein the inlet and outlet tubes are protruded from the outer circumferences of the upper and the lower casings, the inlet tube and the outlet tube are placed in such a way that the central angle with respect to the center of rotation becomes more than one and less than two times the central angle (θ) of one plunger, and the upper rotator and the lower rotator are connected to a driving device to be able to rotate independently.

In the present invention, the driving device includes a first driving unit which, with one plunger positioned between the inlet tube and the outlet tube, rotates with the other plunger in contact with one side of the one plungers to come into contact with the other side of one plunger, so as to position the one plunger between the inlet tube and the outlet tube while shifting the one plunger, and a second driving unit which, with the other plunger positioned between the inlet tube and the outlet tube, rotates with the one plunger in contact with one side of the other plunger to come into contact with the other plunger, so as to position the other plunger between the inlet tube and the outlet tube while shifting the other plunger, and the first driving unit and the second driving unit operate by taking turns.

Namely, with one plunger between the inlet tube and the outlet tube stopped by a clutch stopper on the side of the first driving gear, the front of the other plunger is meshed with the gear of the first drive mechanism at the inlet tube position to be shifted in the normal direction where the one plunger is, pushing out into the inlet tube the liquid medication that is in the cylinder with a shape of about 300 degrees between the one plunger and the other plunger. Simultaneously with this, when the other plunger is shifted in the direction of the back of the one plunger, the back of the other plunger sucks the liquid medication from the inlet tube to fill it in the tubular pipe.

If the other plunger agrees with the back of the one plunger and pushes the liquid medication completely out of the outlet tube and then agrees again with the one plunger, the first driving gear and the second driving gear are meshed simultaneously, so the one plunger and the other plunger that were between the inlet tube and the outlet tube are shifted simultaneously. When the one plunger is shifted toward the inlet tube, and the other plunger reaches between the inlet tube and the outlet tube, the clutch stopper that is on the side of the second driving gear controlling the other plunger fixes the other plunger. So the one plunger, while carrying out the other plunger's shifted action likewise, pushes the liquid medication out at the front and sucks it in at the back.

Repeating the above action, the one plunger, the other plunger and the stopper provides precise control by the size of the tubular cylinder diameter and the control ratio of the driving device to feed a very small quantity or maximum quantity of a liquid medication.

In addition, closers are inserted respectively between the upper casing and the upper rotator, between the lower casing and the lower rotator, between the upper rotator and the lower rotator and between the periphery of the upper casing and the periphery of the lower casing.

Further, in the central portion of the upper casing is formed a through hole through which passes an outer driving gear of the driving device and an inner driving gear positioned in the hollow of the outer driving gear, and in the central portion of the upper rotator are concentrically formed in overlap an outer driving gear joint hole that is joinable with the outer driving gear and an inner driving gear through hole through which the inner driving gear can pass, and in the central portion of the lower rotator is formed an inner driving gear joint hole joinable with the inner driving gear.

Further, the first driving unit and the second driving unit include position retainers installed thereon so as to suppress arbitrary rotation of the pair of the plungers.

In addition, on the outer contour of the surface where the upper casing and the lower casing face each other are formed an upper contour closing seat and a lower contour closing seat respectively, and between the upper contour closing seat and the lower contour closing seat is sandwiched a contour closer.

Further, any one of the upper contour closing seat and the lower contour closing seat is protruded toward the other one.

Further, the flow rate of a liquid medication discharged through the outlet tube is determined by the cross sectional area of the cylinder and the rotation velocity of the plunger driven by the driving device.

Preferably, the driving device includes a housing which forms a body and has a mounting portion on one side of which the cylinder pump is detachably mounted; a driving motor installed in a first bracket fixed on the inside of the housing; a main driving shaft which is rotatably fixed to the first bracket, and is connected to the output shaft of the driving motor to rotate, wherein the main driving shaft is provided with an inner motor-driven gear and an outer motor-driven gear mounted thereon; an inner driving shaft which is rotatably fixed to the a second bracket fixed on the inside of the housing, wherein the inner driving shaft is provided with an inner driven gear meshed with the inner motor-driven gear, and an inner driving gear formed at an end of the journal portion thereof to engage with the upper rotator; and an outer driving shaft which has a boss portion into which the journal portion of the inner driving shaft is inserted, and is rotatably fixed to a second bracket, wherein the outer driving shaft is provided with an outer driven gear mounted thereon corresponding to the inner motor-driven gear meshed with the outer motor-driven gear, and an outer driving gear formed at an end of the boss portion to engage with the lower rotator; and wherein the inner driving gear and the outer driving gear are exposed through the mounting portion; and the inner motor-driven gear and the outer motor-driven gear are identically formed gears, and have gear teeth formed only on a part of the respective outer circumference, wherein the inner motor-driven gear and the outer motor-driven gear are placed in such a way that they have a phase difference of 180° with respect to the main driving shaft.

In addition, the inner motor-driven gear and the outer motor-driven gear have gear teeth formed only on a part of the respective outer circumference so that while rotating the inner driven gear and the outer driven gear $(360-\theta)°$, the inner driven gear and the outer driven gear can be rotated $(360-2 \times \theta)°$ only at a ½ rotation thereof.

Preferably, the cylinder pump further comprises an inner position retainer and an outer position retainer which are installed in the second bracket for maintaining the position of the inner driven gear and the outer driven gear, in a state that the inner driven gear and the outer driven gear are not meshed with the inner motor-driven gear and the outer motor-driven gear, respectively.

Further, each of the inner position retainer and the outer position retainer is provided with an inner boss seat and an outer boss seat having an M-shaped cross section for mounting an inner driven gear boss and an outer driven gear formed on the respective surfaces of the inner driven gear and the outer driven gear.

The cylinder pump according to the present invention can feed a liquid medication at a considerably high degree of precision in spite of simple structure, and can cope with a large range of a liquid medication injection dosage per hour.

In addition, the cylinder pump of the present invention is small in size, so it is easy to carry, and since it is not affected by the height of the receptacle or blood pack, it is possible to maintain the function of the pump without installing a receptacle or blood pack on a pole, so it can substitute the conventional various liquid medication dosage regulators.

Therefore, the cylinder pump occupies a relatively small installation space, and even while a liquid medication is being injected by the cylinder pump, the patient can move freely.

Also, since a liquid medication is controlled directly by the plunger in the cylinder pump, the flow rate per hour can be controlled precisely, so remote control by GPS is possible, and since it is possible to monitor the liquid medication feeding rate for the patient in real time, it is considerably helpful to a reduction of nursing manpower.

Since the liquid medication driving device and operation unit are detachable, the operation unit can be made for disposable type products, so it is possible to feed a liquid medication more safely and sanitarily.

Moreover, since the cylinder pump can be installed without using a pole, it can be installed in various places such as on the bed, floor and wheelchair; since the use of various accessory materials made of fossil fuel such as PVC tubes harmful to the human body and environment is reduced, carcinogenic substances generated during incineration of these products and environmental pollution can be reduced considerably.

BRIEF DESCRIPTION OF DRAWINGS

The above objects, features and advantages of the present invention will become more apparent to those skilled in the related art in conjunction with the accompanying drawings. In the drawings.

DESCRIPTION OF REFERENCE NUMERALS IN DRAWINGS

Figure 1:
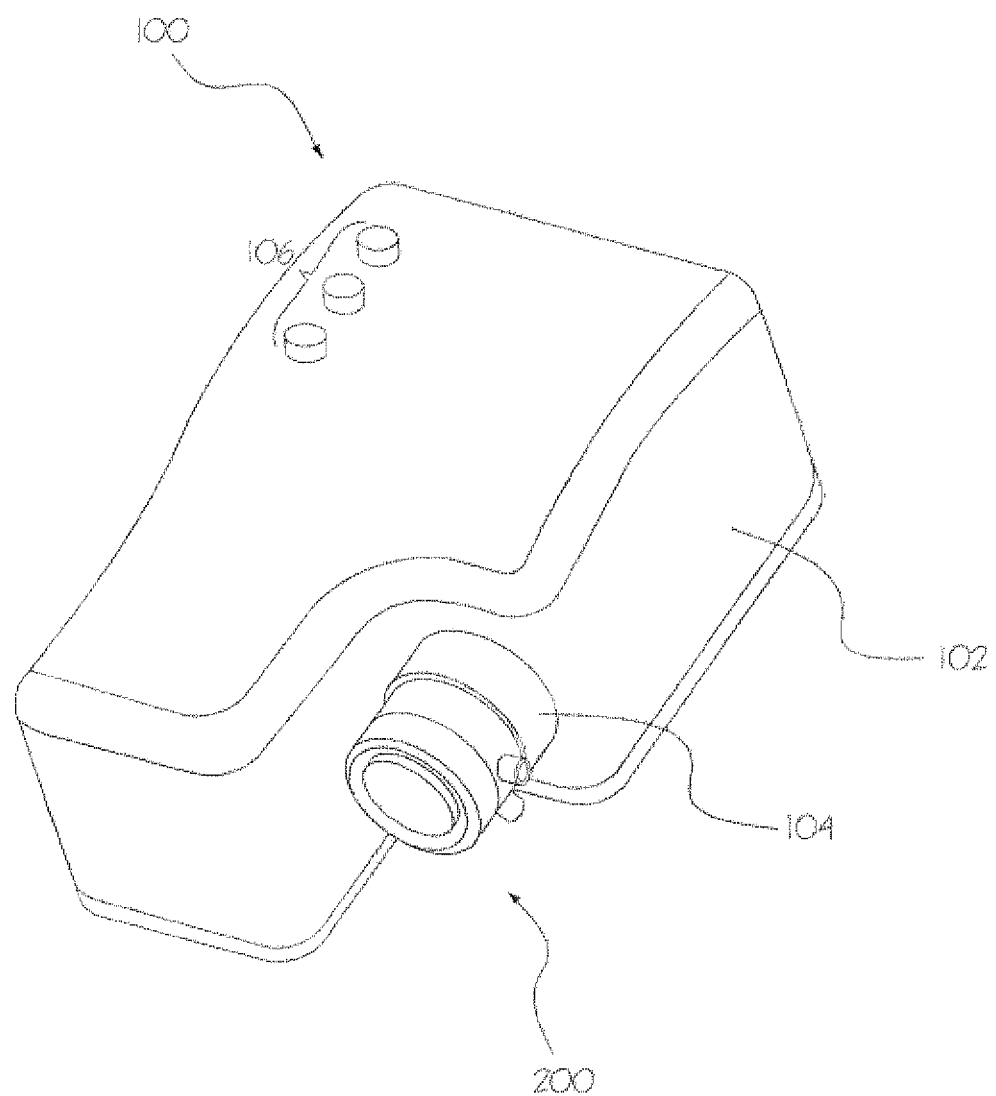
FIG. 1 is a perspective view of an infusion pump according to an embodiment of the present invention.

100: Driving device,
102: Housing
104: Mounting portion,
106: Operation unit
108: Driving motor,
110: First bracket
111: First support,
112: Output shaft
114: Main driving gear,
116: Main reduction gear
118: Main driving shaft,
120: First bearing
122: Second bracket,
124: Inner motor-driven gear
126: Inner driven gear,
127: Inner driven gear boss
128: Outer motor-driven gear,
129: Third bearing
130: Outer driven gear,
131: Outer driven gear boss
132: Second bearing,
133: Inner outer position retainer
134: Fourth bearing,
135: Inner boss seat
136: Fifth bearing,
137: Outer position retainer
138: Sixth bearing,
139: Outer boss seat
140: Second support,
142: Third bracket
143: Enlarged diameter portion,
144: Inner driving shaft
145: Journal portion,
146: Inner driving gear
148: Outer driving shaft
150: Outer driving gear,
200: Operating unit
202: Upper casing,
203: Upper contour closing seat
204: Upper casing body,
205: Upper joint boss
206: Through hole,
208: Upper closing seat
210: Upper rotator slot,
212: Upper cylinder
214: Inlet tube,
216, 276: Outlet tube
218: Upper closer,
220: Upper rotator
222: Upper rotator body,
224: Upper top side closing slot
226: Outer driving gear joint hole
228: Inner driving gear through hole
230: Upper pusher,
232, 234: Upper insert boss
236, 238: Upper bottom side closing boss
240: Upper bottom side closing slot
242: Intermediate closer,
244: Lower rotator
246: Lower rotator body
248, 250: Lower top side closing boss
252: Lower top side closing slot
254: Inner driving gear joint slot
256: Lower pusher,
258, 260: Lower insert boss
262: Lower bottom side closing slot,
263: Lower closer
264: Lower casing,
266: Lower closing seat
268: Lower rotator slot,
270: Lower cylinder
272: Lower casing body,
274: Lower contour closing seat
276: Lower joint boss,
278, 280: Plunger
282, 284: O-ring,
286: Plunger body
288: Insert slot,
290, 292: Insert slot
294: Outer contour closer

DETAILED DESCRIPTION

The present invention will now be described more fully hereinafter with reference to the accompanying drawings forming a part of this specification wherein like reference characters designate corresponding parts in the several views. In the embodiments of the present invention, detailed description of the publicly known functions and configurations that are judged to be able to make the purport of the present invention unnecessarily obscure are omitted.

The cylinder pump according to the present invention does not use a conventional method of squeezing the tube or regulating the flow rate by pushing the plunger, but uses a method of carrying out the inflow and outflow of a liquid medication simultaneously as the two impellers in the tubular cylinder are rotated alternately one by one, namely the principle of the method controlling the flow rate directly.

Accordingly, the method used in the present invention can regulate the flow rate from minute to large by the size and rotation velocity of the cylinder and impeller.

Therefore, the core of the present invention is to regulate the minute flow rate accurately by minute displacement of the impeller at the operation unit.

In particular, the cylinder pump according to the present invention is composed of a driving device and an operation unit detachably mounted to the driving device. Accordingly, the driving device can be used permanently, and the operation unit can be used disposably.

FIG. 1 is a perspective view of the cylinder pump according to an embodiment of the present invention. The cylinder pump consists of a driving device 100 and an operation unit 200. As mentioned above, the operation unit 200 is detachably assembled to the driving device 100 for disposable type products.

The driving device 100 includes a first driving unit, which with the one plunger, positioned between the inflow pipe and the outflow pipe, rotates with the other plunger in contact with one side of the one plunger and positions the one plunger between the inflow pipe and the outflow pipe while shifting the one plunger in contact with the other side of the one plunger, and a second driving unit, which with the other plunger positioned between the inflow pipe and the outflow pipe, rotates with the one plunger in contact with one side of the other plunger and positions the other plunger between the inflow pipe and the outflow pipe while shifting the other plunger in contact with the other side of the other plunger, and the first driving unit and the second driving unit operate by taking turns.

Accordingly, the driving device 100 is provided with a housing 102, and a mounting portion 104 on one side of the housing 102 for mounting the operating unit 200, and in the mounting portion 104 are placed an inner driving gear 146 and an outer driving gear 150 of the driving unit to be described later.

On one side the housing 102 is placed an operation unit 106 for operating the operating unit 200 as you please.

Figure 2:
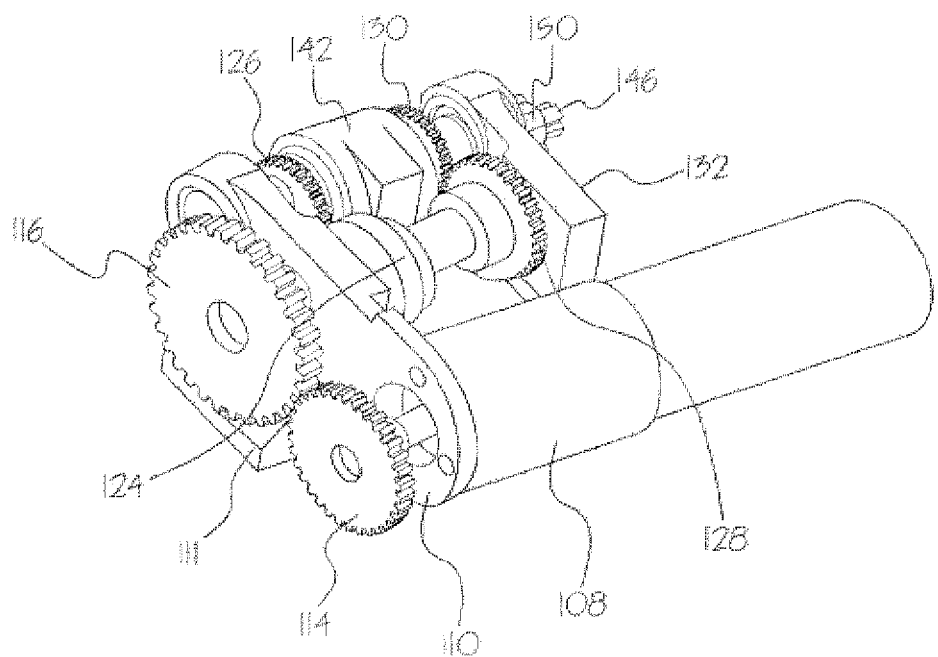
FIG. 2 is a perspective view showing the driving unit in the driving device of the cylinder pump of FIG. 1.
Figure 3:
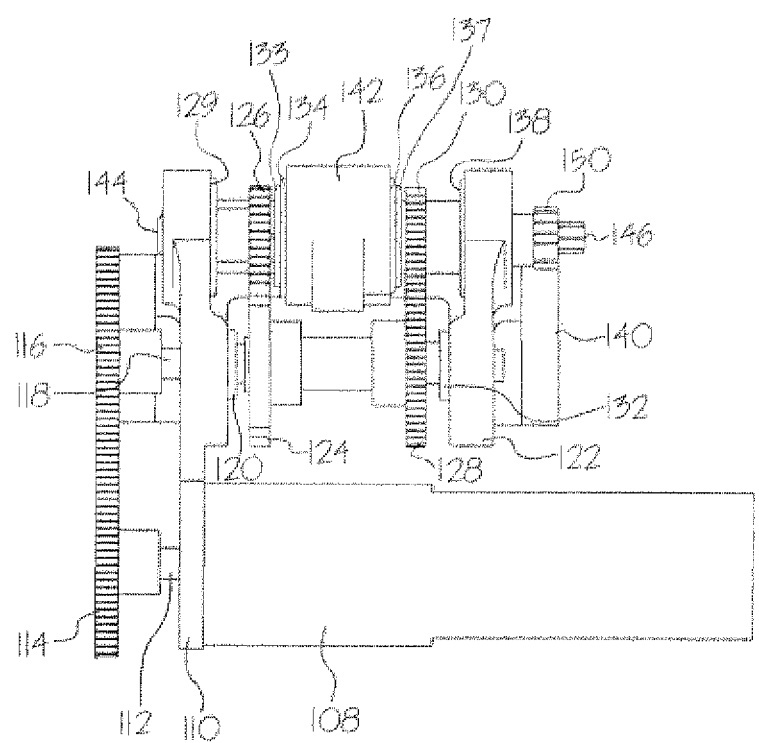
FIG. 3 is a front view of the driving unit shown in FIG. 2.
Figure 4:
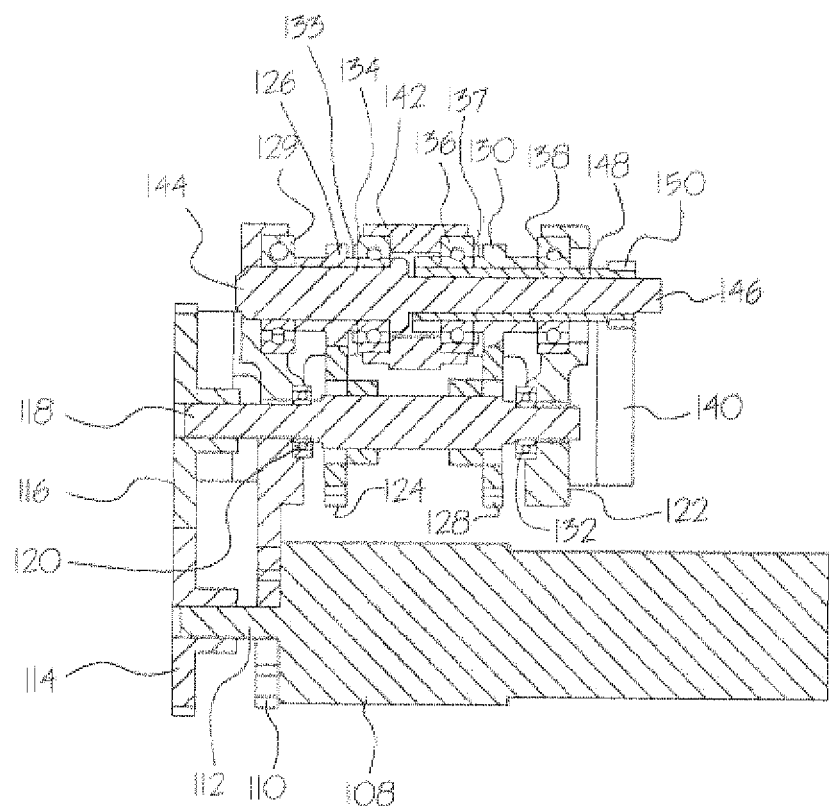
FIG. 4 is a sectional view of the driving unit shown in FIG. 2.

FIG. 2 is a perspective view of the driving unit contained in the driving device 100 of the cylinder pump, and FIG. 3 is a front view of the driving unit, and FIG. 4 is a sectional view of the driving unit.

The driving means of the driving unit is a driving motor 108, which drives the inner driving gear 146 and the outer driving gear 150 respectively through a plurality of gear trains.

The driving motor 108 is fixed to the first bracket 110, and at one end of the output shaft 112 of the driving motor 108 is monolithically installed a main driving gear 114. The main driving gear 114 is meshed with a main reduction gear 116 to increase the torque ratio. Namely, the main reduction 116 has more teeth than the main driving gear 114, so it increases the torque through rotational reduction. Due to this, the load applied to the driving motor 108 can be reduced, and the selection range of the driving motor 108 according to capacity broadens.

The main reduction gear 116 is monolithically installed at one end of the main driving shaft 118. As shown in FIG. 3, opposed end portions of the main driving shaft 118 are rotatably mounted to the a first bracket 110 and a second bracket 122 through a first bearing 120 and a second bearing 132, respectively.

The first bracket 110 and the second bracket 122 are fixed on the housing 102. And in order to support the first bracket 110 and the second bracket 122 and fix them to the housing 102, a first support 111 and a second support 140 may be additionally provided.

And on the outer circumference of the main driving shaft 118 are monolithically fixed the inner motor-driven gear 124 and the outer motor-driven gear 128. Accordingly, the rotation velocity in the inner electrical gear 124 and the outer motor-driven gear 128 are equal.

Figure 5:
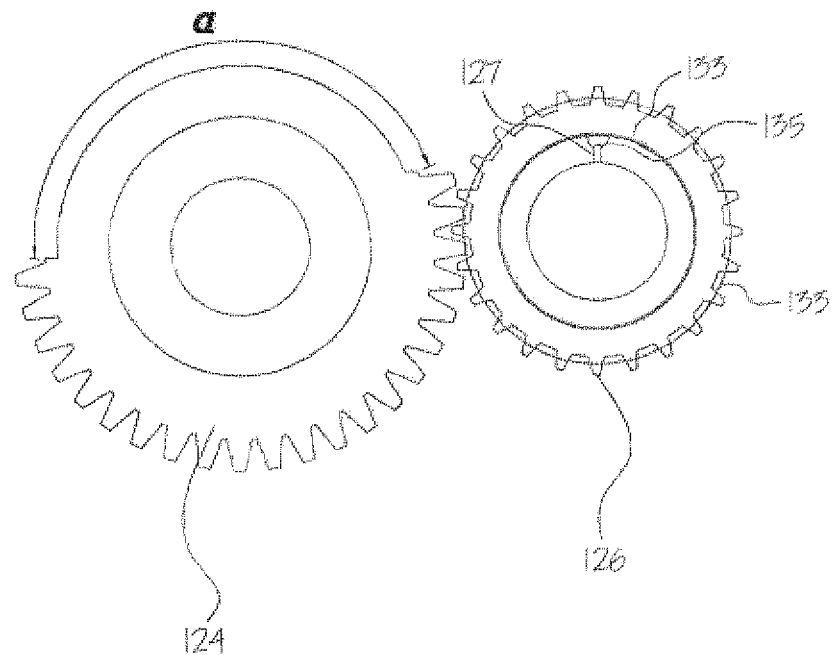
FIG. 5 is a schematic view of the inner motor-driven gear and inner driven gear that rotate the inner driving gear in the driving unit of FIG. 2.
Figure 6:
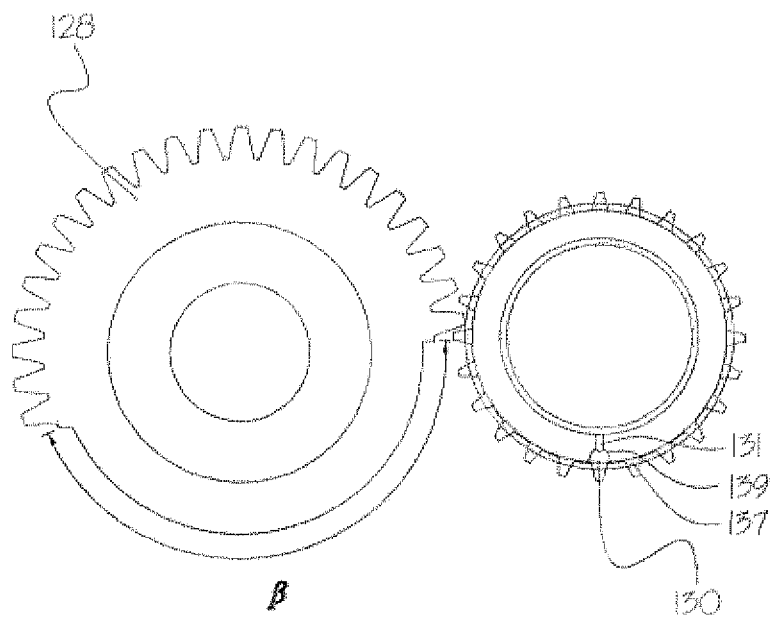
FIG. 6 is a schematic view of the outer motor-driven gear and outer driven gear that rotate the outer driving gear in the driving unit of FIG. 2

The inner motor-driven gear 124 is meshed with the inner driven gear 126 as shown in FIG. 5, and the outer motor-driven gear 128 is meshed with the outer driven gear 130 as shown in FIG. 6.

Figure 7:
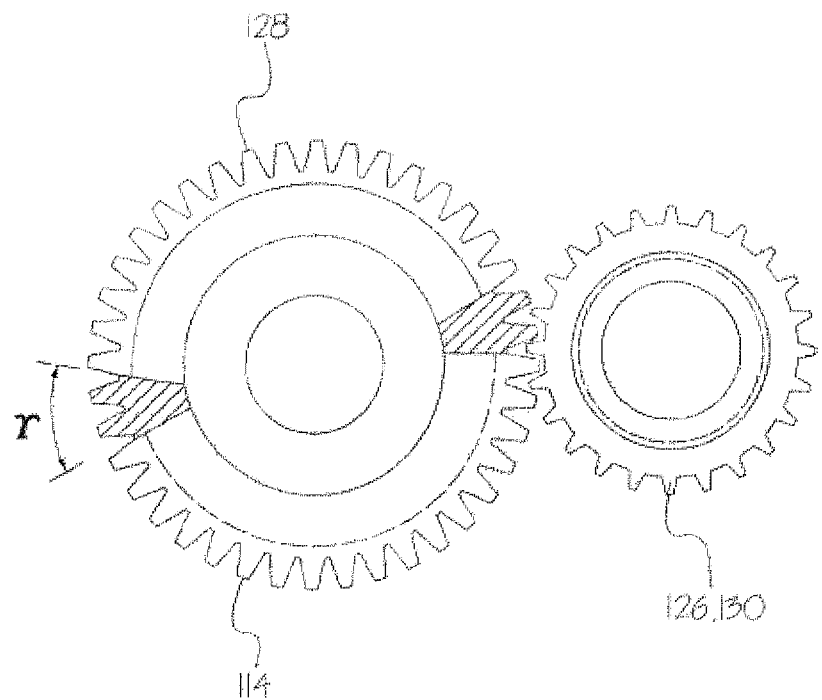
FIG. 7 is a schematic view showing by overlapping FIG. 5 and FIG. 6.
Figure 8:
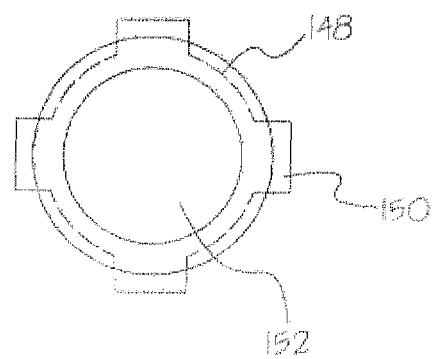
FIG. 8 is a left side view of an inner driving gear shaft with an inner driving gear formed thereon in the driving unit of FIG. 2.
Figure 9:
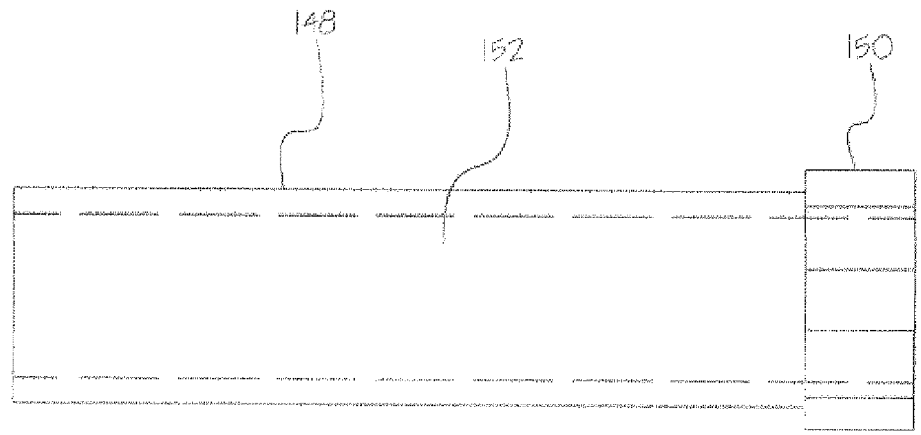
FIG. 9 is a front view of the inner driving gear shaft shown in FIG. 8
Figure 10:
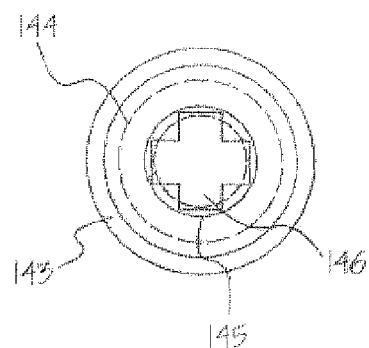
FIG. 10 is a left side view of the outer driving gear shaft with the outer driving gear formed thereon in the driving unit of FIG. 2.
Figure 11:
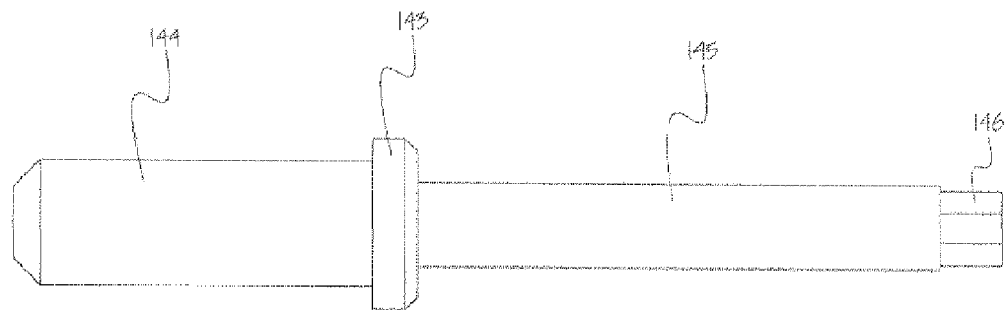
FIG. 11 is a front view of the outer driving gear shaft shown in FIG. 10
Figure 12:
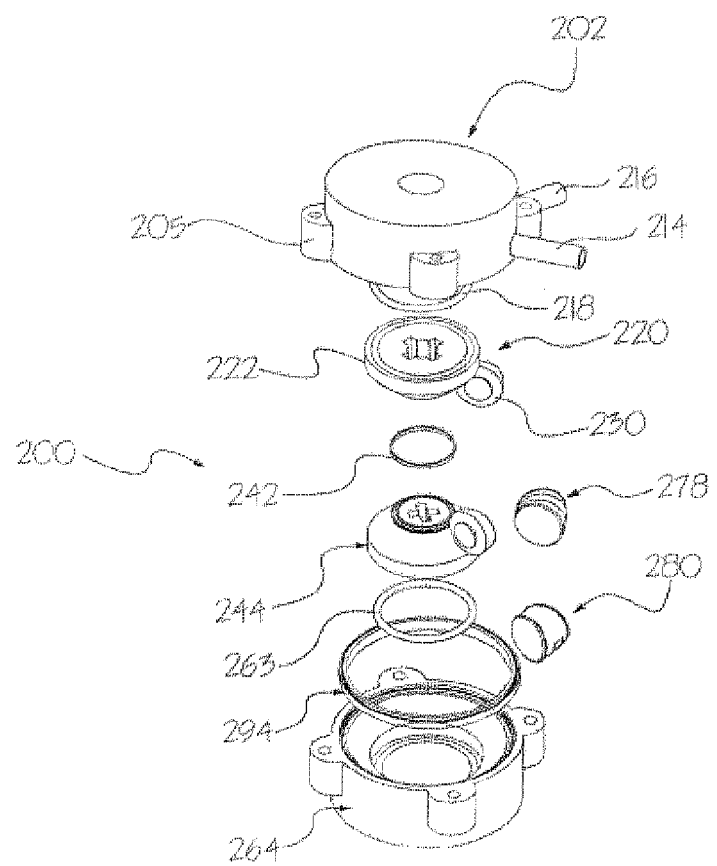
FIG. 12 is an exploded perspective view of the operating unit of the cylinder pump shown in FIG. 1.

The inner motor-driven gear 124 and the outer motor-driven gear 128 are the same gears, but when fixed on the main driving shaft 118, and when projected as shown in FIG. 7 based on the main driving shaft 118, they are installed in mutually symmetrical positions.

First will be described the relation between the inner motor-driven gear 124 and the inner driven gear 126. As shown in FIG. 5, the inner motor-driven gear 124 has only 22 teeth formed on the circumference on which 40 teeth can be seated, and the area of angle α, which is the remaining portion, has no teeth. Accordingly, only 22 teeth of the inner motor-driven gear 124 are meshed with the inner driven gear 126 and rotate the inner driven gear 126.

The inner driven gear 126 has 24 teeth formed on the circumference thereof. Accordingly, the central angle occupied by one tooth is 15°, and while the inner motor-driven gear 124 makes one rotation the inner driven gear 126 can rotate 330°. Namely, while the inner motor-driven gear makes one rotation, the inner driven gear 126 rotates by 30° less, which is the central angle occupied by two teeth. At this time, the 30° angle of rotation that the inner driven gear 126 lacks is equal to the central angle occupied by plungers 278 and 280 to be described later. Accordingly, as the central angle occupied by the plungers 278 and 280 decreases, the angle of rotation of the inner driven gear 126 per rotation of the inner motor-driven gear 124 increases.

After all, the diameter and the number of teeth of the inner motor-driven gear 124 and the diameter and the number of teeth of the inner driven gear 126 are sufficient if they can rotate the inner driven gear 126 during one rotation of the inner motor-driven gear 124 as much as the size resulting from subtracting from 360° the central angle occupied by plungers 278 and 280, and if necessary, more gears may be used.

Next will be explained the relation between the outer motor-driven gear 128 and the outer driven gear 130. As shown in FIG. 6, the outer motor-driven gear 128 has only 22 teeth formed on the circumference that can have 40 teeth seated thereon, and there are no teeth in the area of angle β, which is the remaining portion. Accordingly, only 22 teeth of the outer motor-driven gear 128 are meshed with the outer driven gear 130 to rotate the outer driven gear 130.

The outer driven gear 130 has 24 teeth formed on the circumference thereof. Accordingly, the central angle occupied by one tooth is 15°, and while the outer motor-driven gear 128 makes one rotation, the outer driven gear 130 can rotate 330°. Namely, while the outer motor-driven gear makes one rotation, the outer driven gear 130 rotates by 30° less, which is the central angle occupied by two teeth. At this time, the 30° angle of rotation that the outer driven gear 130 lacks is equal to the central angle occupied by plungers and 278 and 280 to be described later. Accordingly, according as the central angle occupied by plungers 278 and 280 decreases, the angle of rotation of the outer driven gear 130 per rotation of the outer motor-driven gear 128 increases.

After all, the diameter and the number of teeth of the outer motor-driven gear 128 and the diameter and the number of teeth of the outer driven gear 130 are sufficient if they can rotate the inner driven gear 130 during one rotation of the inner motor-driven gear 128 as much as the size resulting from subtracting from 360° the central angle occupied by plungers 278 and 280, and if necessary, more gears may be used.

And the inner driven gear 126 and the outer driven gear 130 rotate independently without affecting each other. For this, the inner driven gear 126 is installed on the inner driving shaft 144, and on the outer driven gear 130 is formed a boss portion 152 into which the journal portion 145 of the inner driving shaft 144 is inserted. As a result, the outer driven gear 130 can rotate independently of the inner driven gear 126 due to the sliding rotation of the boss portion 152 and the journal portion 145.

The inner driving shaft 144 is rotatably mounted on the first bracket 110 through a third bearing 129 and one side of a third bracket 142 through a fourth bearing 134. The outer driving shaft 148 is rotatably mounted on the other side of the third bracket 142 through a fifth bearing 136 and on the second bracket 122 through a sixth bearing 138. The third bracket 142 is fixed on the housing 102.

In addition, at one end of the right side of the inner driving shaft 144 is formed the inner driving gear 146, and on one end of the right side of the outer driving shaft 148 is formed the outer driving gear 150, and as shown in FIG. 2 and FIG. 3, the inner driving gear 146 is installed so as to be protruded to the right side more than the end portion of the outer driving gear 150.

In the embodiment of the present invention, both the outer driving gear 150 and the inner driving gear 146 are formed in a cross shape, but the shape of the outer driving gear 150 and the inner driving gear 146 are not particularly limited thereto.

And on the third bracket 142 are installed the inner and outer position retainers 133 and 137 that can prevent arbitrary rotation of the inner driving gear 146 and the outer driving gear 150.

In the inner and outer position retainers 133 and 137 are formed an inner boss seat 135 and an outer boss seat 139 to match an inner driven gear boss 127 and an outer driven gear boss 131 formed respectively on the surfaces (upper surfaces or lower surfaces) of the inner driven gear 126 and outer driven gear 130, as shown in FIGS. 5 and 6.

The inner driven gear boss 127 and the outer driven gear boss 131 have protruded structures in a shape of a bar whose radial outside end portion is rounded, and the inner boss seat 135 and the outer boss seat 139 are formed roughly in an M shape for the inner and outer driven gear bosses 127 and 132 to be mounted. The M shapes of the inner and outer driven gear bosses 127 and 132 are also rounded, so that the inner driven gear boss 127 and the outer driven gear boss 131 are formed detachably from the inner and outer driven gear bosses 127 and 132 in case external force is applied.

The driving device 100 is composed basically as mentioned above. Next, the output form of the driving device 100, namely, the operating mode of the outer driving gear 150 and the inner driving gear 146 according to the rotation of the driving motor 108, will be described.

Rotation of the driving motor 108 is transmitted to the main reduction gear 116 via the main driving gear 114 to cause speed reduction and torque increase. And the main driving shaft 118 is rotated by rotation of the main reduction gear 116, and the inner motor-driven gear 124 and the outer motor-driven gear 128 rotate at an angular velocity the same as the main driving shaft and in the same direction.

At this time, suppose the state of FIG. 7 is an initial state, then while the main driving shaft 118 makes a ½ rotation clockwise, the outer motor-driven gear 128 rotates the outer driven gear 130 by 300° (that is, as much as 20 teeth). And the inner motor-driven gear 126 rotates the inner driven gear 126 by 30° (that is, as much as two teeth) only at the time of starting; after that it does not rotate the inner driven gear 126.

Next, while the main driving shaft 118 makes an additional ½ rotation clockwise in this state, the inner motor-driven gear 124 rotates the inner driven gear 126 by 300° (that is, as much as 20 teeth). And the outer motor-driven gear 128 rotates the outer driven gear 130 by 30° (that is, as much as two teeth) only at the initial state; after that it does not rotate the outer driven gear 130.

Namely, while the inner driven gear 128 and the outer driven gear 130 rotate 300° respectively, only either one rotates, but in the area γ that is oblique-lined in FIG. 7 (that is, the area as much as two teeth, 30°), they rotate simultaneously.

Accordingly, the inner driven gear 126 and the outer driven gear 130 carry out the next actions repetitively by the rotation of the driving motor 108:
1) The inner driven gear 126 only rotates 300°;
2) The inner driven gear 126 and the outer driven gear 130 rotate 30° simultaneously;
3) The outer driven gear 130 only rotates 300°; and
4) The inner driven gear 126 and the outer driven gear 130 rotate 30° simultaneously.

Accordingly, the inner driven gear 126, the inner driving gear 146 formed monolithically with the outer driven gear 130 by the outer driving shaft, and the outer driving gear 150 respectively rotate independently.

However, in the process that the inner driving gear 146 and the outer driving gear 150 respectively rotate plungers 278 and 280 to be described later, negative pressure or positive pressure acts between a pair of the plungers 278 and 280. Therefore, it is preferable to additionally install the position retainers 133 and 137 as mentioned above on the outer driving shaft 148 and the inner driving shaft 144 on which the inner driving gear 146 and the outer driving gear 150 are installed, so that the angle positions of the plungers 278 and 280 are not varied by the negative pressure and positive pressure between the pair of the plungers 278 and 280.

Accordingly, unintended variation of angle positions of the plungers 278 and 280 due to the position retainers 133 and 137 do not occur, and it is possible to suppress the backlash between the inner motor-driven gear 124 and the inner driven gear 126 where engagement and separation of the gear teeth occur repeatedly and between the outer motor-driven gear 128 and the outer driven gear 130.

Next, the operating unit 200 detachably mounted to the driving device 100 of cylinder pump will be described. The operating unit 200 is operated by the rotation of the inner driving gear 146 and the outer driving gear 150 of the driving device 100. Here, the rotation of the inner driving gear 146 and the outer driving gear 150 can be operated by the above-mentioned driving device 100, but as long as the above-mentioned motion characteristics are satisfied, the composition of the driving device 100 is not particularly limited.

The operating unit 100 basically includes an upper casing 202 and a lower casing 264 that make the body, an upper rotator 222 inserted into the upper casing 202, and a lower rotator 244 inserted into the lower casing 264.

In the upper casing 202 are formed an inlet tube 214 for a liquid medication to be introduced into the operating unit 100 and an outlet tube 216 for feeding a liquid medication to the liquid medication tube, etc. The inlet tube 214 and the outlet tube 216 are formed in the lower casing 264, or they can be formed half and half in the upper casing 202 and the lower casing 264, respectively.

And in the upper casing 202 and the lower casing 264 are formed an upper cylinder 212 and a lower cylinder 270 respectively, and a cylinder in the shape of one tube is made by the upper casing 202, the lower casing 264, and the outer circumferences of the upper rotator 220 and the lower rotator 244. And in the cylinder are formed the inlet tube 214 and the outlet tube 216 in such a way that they communicate with each other.

Figure 13:
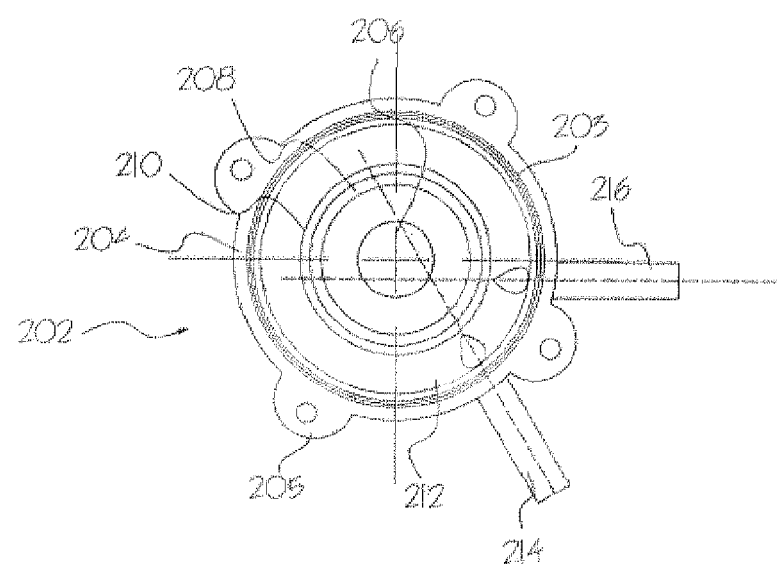
FIG. 13 is a bottom view of the upper casing of the operating unit shown in FIG. 12.
Figure 20:
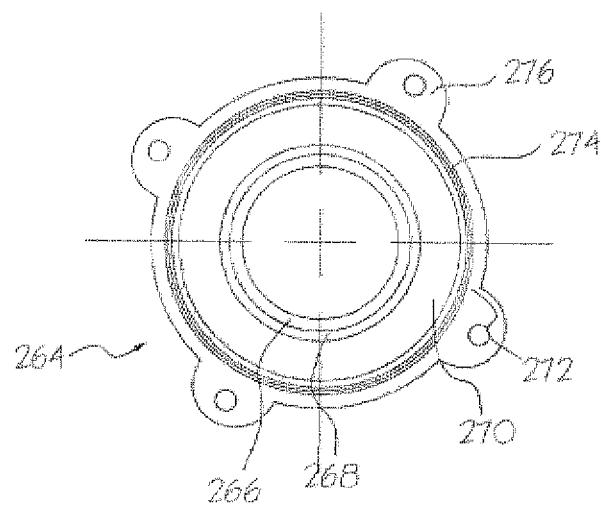
FIG. 20 is a plan view of the lower casing in the operating unit of FIG. 12.

The inlet tube 214 and the outlet tube 216 are deviated as much as ½ of the thickness with respect the center of the upper casing 202 and the lower casing 264, as shown in FIG. 13 and FIG. 20. And the angle between the inlet tube 214 and the outlet tube 216 is 30°. This agrees with the central angle 30° occupied by plungers 278 and 280 to be described later, and the purpose of this is not to close the inlet tube 214 and the outlet tube 216 when either of the plungers 278 and 280 is positioned between the inlet tube 214 and the outlet tube 216.

Figure 14:
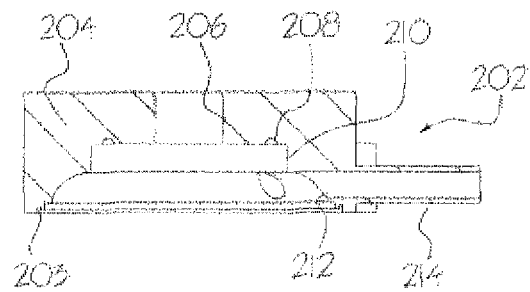
FIG. 14 is a front sectional view of the upper casing shown in FIG. 13.

The upper casing 202 includes, as shown in FIGS. 13 and 14, an upper casing body 204, which is a rotator, a through hole 206 formed in such a way that the outer driving gear 150 and the inner driving gear 146 can pass through in the central portion, an upper rotator slot 210 into which the upper rotator 220 is inserted, the upper cylinder 212 forming a moving space for plungers 278 and 280, an upper contour closing seat 203 formed in the periphery of the upper casing body 204, the inlet tube 214 and the outlet tube 216.

And in the upper rotator slot 210 is formed an upper closing seat 208 for an upper closer 218 to be positioned.

Corresponding to the upper contour closing seat 203 of the upper casing 202 is formed a lower contour closing seat 274 in the lower casing 264, and an outer contour closer 294 is placed between the upper contour closing seat 203 and the lower contour closing seat.

It is preferable that either of the upper contour closing seat 203 and lower contour closing seat 274 is formed in a protruded shape so as to improve closing force by pressurizing the contour closer 294 to the other side.

In addition, upper joint bosses 205 are formed outward of the upper casing body 204, and lower joint bosses 276 are formed outward of the lower casing body 272 of the lower casing 264, so the upper casing 202 and the lower casing 264 can be engaged by a fastening means such as bolts and nuts.

Figure 15:
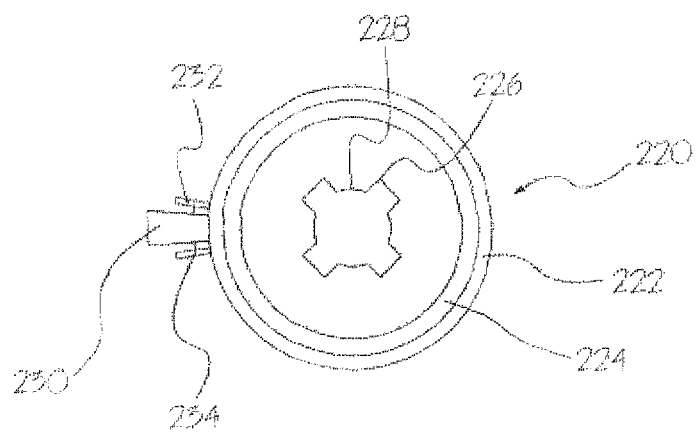
FIG. 15 is a plan view of the upper rotator in the operating unit shown in FIG. 12.
Figure 16:
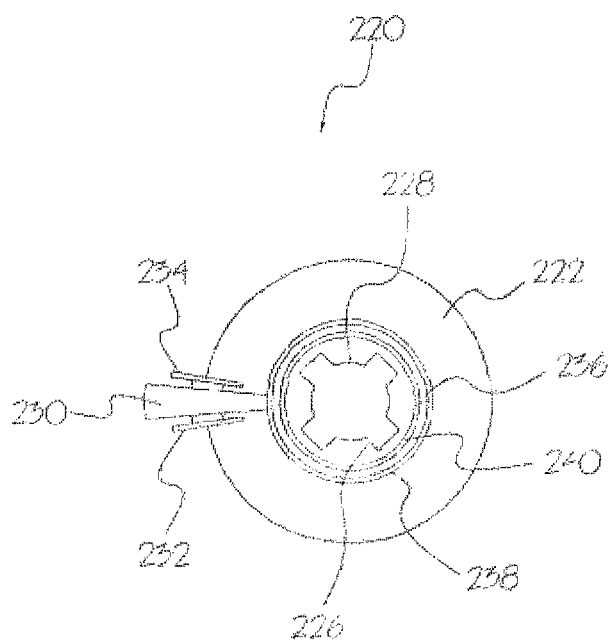
FIG. 16 is a bottom view of the upper rotator shown in FIG. 15

The upper rotator 220 includes, as shown in FIG. 15 and FIG. 16, an upper rotator body 222 whose top side is inserted into the upper rotator slot 210 and whose lower side is roundly formed so as to form the upper portion of the cylinder together with the upper cylinder 212, and an upper pusher 230 which is formed monolithically on one side of the upper rotator body 222.

On the top side of the upper rotator 220 is formed an upper top side closing slot 224 where the upper closer 218 is positioned, and on the bottom side of the upper rotator 220 are protruded upper bottom side closing bosses 236 and 238 at intervals on the inside and outside of an upper bottom side closing slot 240 so as to form the upper bottom side closing slot 240 where the intermediate closer 242 is positioned.

On both sides of the upper pusher 230 are formed upper insert bosses 232 and 234 so as to make it easy to fix on the plunger 278.

In addition, an outer driving gear joint hole 226 for the outer driving gear 150 to be engaged therewith, and an inner driving gear through hole 228 are formed in the center of the upper rotator 220 so that the inner driving gear 146 passes there through concentrically with the outer driving gear joint hole 226. At this time, it is preferable that the outer driving gear joint hole 226 has a cross sectional area equal to or smaller than the outer driving gear 150 so that the outer driving gear is tightly fixed. And it is preferable that the inner gear through hole 228 has a cross section larger than the maximum diameter of the inner driving gear 146 so as to reduce contact area.

The upper casing 202 includes, as shown in FIG. 13 and FIG. 14, an upper casing body 204, which is a rotator, a through hole 206 formed in such a way that the outer driving gear 150 and the inner driving gear 146 can pass through in the central portion of the upper casing body 204, an upper rotator slot 210 into which the upper rotator 220 is inserted, and an upper cylinder 212 forming a moving space for the plungers 278 and 280, the inlet tube 214 and the outlet tube 216.

As mentioned above, in the upper rotator slot 210 is formed the upper closing seat 208 for the upper closer 218 to be positioned.

Figure 17:
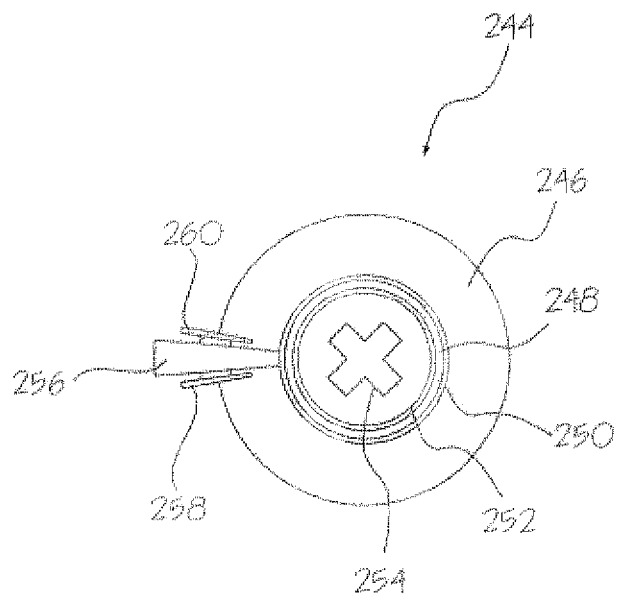
FIG. 17 is a plan view of the lower rotator in the operating unit of FIG. 12.
Figure 18:
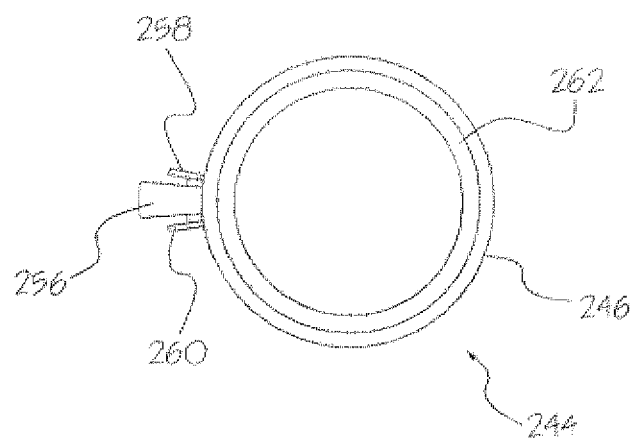
FIG. 18 is a bottom view of the lower rotator of FIG. 17.

The lower rotator 244 includes, as shown in FIG. 17 and FIG. 18, a lower rotator body 246 whose top side is roundly formed so as to form the lower portion of the cylinder together with the lower cylinder 270 and whose lower side is inserted into the lower rotator slot 268, and a lower pusher 256 formed monolithically on one side of the lower rotator body 246.

On the upper side of the upper rotator 244 are protruded lower top side closing bosses 248 and 250 at intervals on the inside and outside of a lower top side closing slot 252 so as to form the lower top side closing slot 252 where the middle closer 242 is positioned, and on the lower side of the lower rotator 244 is formed a lower bottom side closing slot 262 where a lower closer 263 is positioned.

On both sides of the lower pusher 256 are formed lower insert bosses 258 and 260 so as to make it easy to fix on the plunger 280.

And in the center of the lower rotator 244 is formed an inner driving gear joint slot 254 for joining an inner driving gear 146. At this time, it is preferable that the inner driving gear slot 254 has a cross sectional area equal to or smaller than the inner driving gear 146 so that the inner driving gear 146 is tightly fixed.

Figure 19:
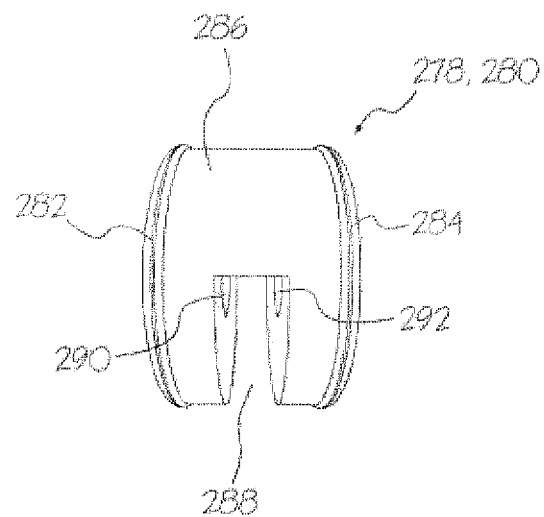
FIG. 19 is a front view of the plunger in the operating unit of FIG. 12.

Next, the both ends of the plungers 278 and 280 are fixed on the upper pusher 230 and the lower pusher 256 as shown in FIG. 19. The plungers 278 and 280 have cross sectional areas equal to that of the cylinder which is formed, by being bent at the same radius of curvature, and its central angle is 30° as mentioned above. The central angle of the plungers 278 and 280 are the same as the central angle between the inlet tube 214 and the outlet tube 216.

And in the center of the plungers 278 and 280 is formed an insert slot 288 into which the upper pusher 230 or the lower pusher 256 is inserted, and on the left and right sides of the insert slot 288 are formed insert slots 290 and 292 which are engaged with upper insert bosses 232 and 234 or the lower insert bosses 258 and 260. And on both sides of the outer circumference of the plungers 278 and 280 are inserted O-rings 282 and 284, so that the plungers 278 and 280 can come into close contact with the inner wall of the cylinder.

Figure 21:
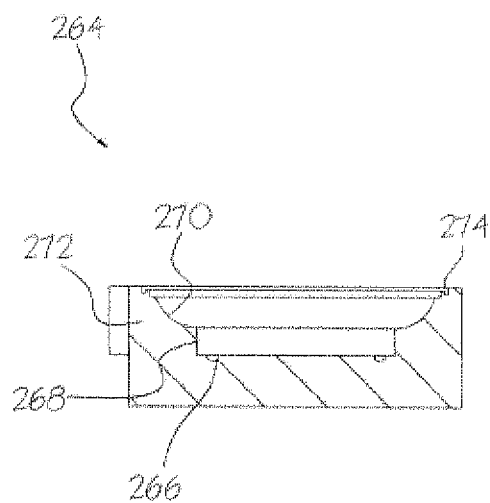
FIG. 21 is a front sectional view of the lower casing shown in FIG. 20.

The lower casing 264 includes, as shown in FIG. 20 and FIG. 21, a lower casing body 272, which is a rotator, a lower rotator slot 268 into which the lower rotator 244 is inserted, and a lower cylinder 270 which forms a moving space for the plungers 278 and 280.

And in the lower rotator slot 268 is formed a lower closing seat 266 where the lower closer 263 can be positioned.

Around the lower casing body 272 is formed the lower contour closing seat 274 as mentioned above, and outward of the upper casing body 204 are formed the upper joint bosses 205, and outward of the lower casing body 272 are formed the lower joint bosses 276 to correspond to the upper joint bosses 205 of the upper casing 202.

The operating unit 200 is composed basically as mentioned above, and below will be described the assembled state and the operating method.

Figure 22:
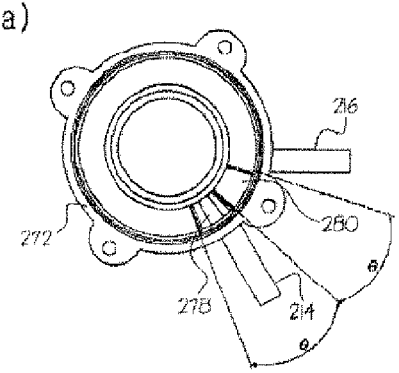
FIG. 22 is a view schematically showing the operating sequence of the operating unit after assembling the operating unit of FIG. 12.
Figure 22:
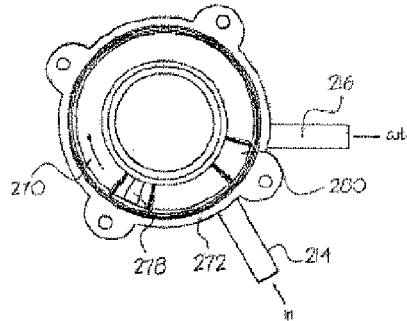
Figure 22:
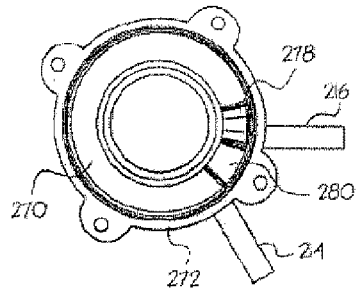
Figure 22:
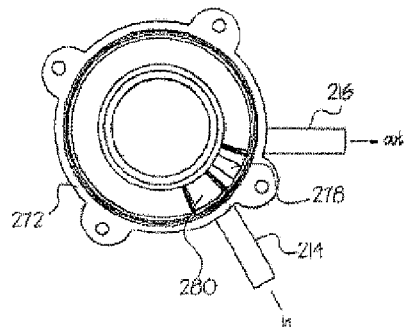
Figure 22:
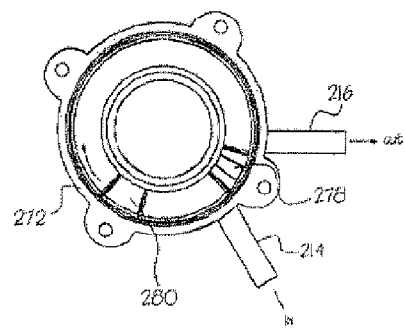
Figure 22:
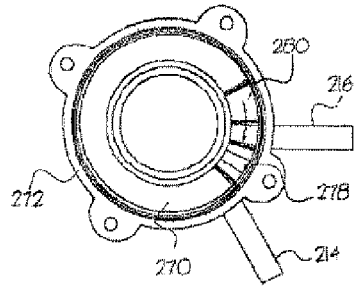
Figure 22:
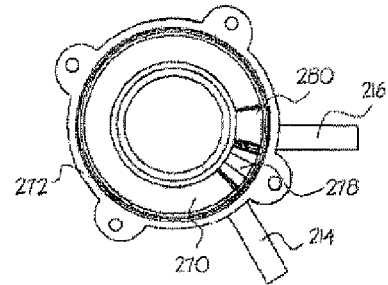
Figure 22:
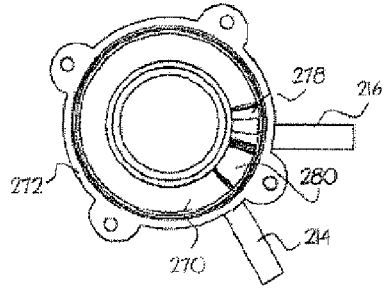

FIG. 22 is a view schematically showing the sequence of operation of the operating unit 100, after assembling the upper rotator 222 and lower rotator 244 of the operating unit 200.

As shown in FIG. 22, description will be given based on the lower casing 264, and the inlet tube 214 and outlet tube 216 are installed in the upper casing 202, but to make it easy to understand, it is illustrated in such a way that it communicates with the lower casing 264. And the positions of the outlet tube and the inlet tube are for the case that the plungers 278 and 280 rotate clockwise; if the direction of rotation of the plungers 278 and 280 is counterclockwise, the drawing symbol 216 becomes the inlet tube and the drawing symbol 214 becomes the outlet tube.

The product on the market is in a sealed state, and the plungers 278 and 280 shown in FIG. 22a rotated a little further clockwise, so the plungers 278 and 280 have closed the outlet tube 216 and the inlet tube 214.

And the operation start state is, as shown in FIG. 22a, a state in which any one plunger 280 is positioned between the inlet tube 214 and the outlet tube 216 and the other plunger 278 has closed the inlet tube 214. The operation state in a sealed condition starts through the operation of the driving device 100.

Next, when the plunger 280 starts to rotate clockwise as shown in FIG. 22b, negative pressure is generated in the cylinder, such that a liquid medication is introduced into the cylinder through the inlet tube 214. And when it continues to rotate clockwise, the plunger 278 comes into contact with the plunger 280 which is positioned between the outlet tube 216 and the inlet tube 214. Namely, the plunger 278 rotates 300°. In this state, the plunger 278 has closed the outlet tube 216.

And the preceding plunger 280 and the following plunger 278 rotate 30° clockwise simultaneously. Accordingly, as shown in FIG. 22d, the following plunger 278 is positioned between the outlet tube 216 and the inlet tube 214. In this state, as shown in FIG. 22e and FIG. 22f, according as the plunger 280 rotates clockwise, the liquid medication in the cylinder that is positioned in the direction of rotation (clockwise) ahead of the plunger 280 is discharged through the outlet tube 216. At the same time, the liquid medication flows into the rear side of the plunger 280 through the inlet tube 214 to fill in the cylinder. In other words, discharge and inlet of the liquid medication in the cylinder occur simultaneously by the rotating plunger 280.

And when the plunger 280 continues to rotate clockwise, the plunger 280, as shown in FIG. 22g, comes into contact with the plunger 278 positioned between the outlet tube 216 and the inlet tube 214. Namely, the plunger 280 rotates 300°. In this state, the plunger 280 has closed the outlet tube 216.

And the preceding plunger 278 and the following plunger 280 rotate 30° clockwise simultaneously and returns again to the state as shown in FIG. 22a.

As mentioned above, if the plungers 278 and 280 make one rotation respectively, they carry out again the actions shown in FIGS. 22a to 22g repetitively. Accordingly, the operating unit 200 can carry out the feeding of a liquid medication continuously, and minute regulation of the feed of the liquid medication is possible by controlling the rotation velocity of the plungers 278 and 280.

Below will be described the operating process of the operating unit 200 in relation to the operating device 100. The plunger 280 is connected to the inner driving gear 146, and the plunger 278 is connected to the outer driving gear 150

Accordingly, when the outer driving gear 150 starts first to rotate in a state of FIG. 22a and the outer driving gear 150 rotates 300°, the plunger 278 rotates clockwise and comes into contact with the plunger 280 positioned between the outlet tube 216 and the inlet tube 214, as shown in FIG. 22c. In this state, when the outer driving gear 150 and the inner driving gear 146 rotate 30° simultaneously as mentioned above, the plunger 278 comes to be positioned between the outlet tube 216 and the inlet tube 214, and the plunger 280 is pushed out toward the inlet tube 214.

And when the inner driving gear 146 rotates 300° again, the plunger 280 rotates 300° clockwise, so it comes into contact with the plunger 278 positioned between the outlet tube 216 and the inlet tube 214, as shown in FIG. 22g. In this state, when the outer driving gear 150 and the inner driving gear 146 rotate 30° simultaneously as mentioned above, the plunger 280 comes to be positioned between the inlet tube 214 and the outlet tube 216, and the plunger 278 is pushed out toward the inlet tube 214.

Accordingly, by the alternate rotation of the inner driving gear 146 and the outer driving gear 150 of the operating device 100, the above-mentioned process is repeated, so that the feeding of a liquid medication of the operating unit 200 is made continuously.

And the displacement of the plungers 278 and 280 due to positive pressure and negative pressure generated between the plungers 278 and 280 can be controlled by the position retainers 133 and 137 mentioned above, so it is possible to feed a liquid medication constantly at all times.

Although the present invention has been described in connection with the exemplary embodiments illustrated in the drawings, it is only illustrative. It will be understood by those skilled in the art that various modifications and equivalents can be made to the present invention. Therefore, the true technical scope of the present invention should be defined by the appended claims.

What is claimed is:

1. A cylinder pump comprising:
a cylindrical upper casing inside which an upper rotator is rotatably inserted; and
a cylindrical lower casing which is engaged with the upper casing and inside which a lower rotator that is in rotation sliding contact with the upper rotator is rotatably inserted, wherein an inner wall of the upper casing, a lower outer circumference of the upper rotator, an inner wall of the lower casing, and an upper outer circumference of the rotator form a single tubular cylinder, the upper rotator and the lower rotator include first and second plungers mounted thereon respectively, which make rotation in the tubular cylinder which is closed by the first and second plungers, the tubular cylinder is provided with an inlet tube for a liquid medication to be flowed in and an outlet tube for the liquid medication to be flowed out, wherein the inlet and outlet tubes are protruded from outer circumferences of the upper and the lower casings, the inlet tube and the outlet tube are placed in such a way that a central angle with respect to a center of rotation becomes more than one and less than two times a central angle ($\theta$) of one of the first and second plungers, and the upper rotator and the lower rotator are connected to a driving device to be able to rotate independently.

2. The cylinder pump of claim 1, wherein closers are inserted respectively between the upper casing and the upper rotator, the lower casing and the lower rotator, the upper rotator and the lower rotator and a periphery of the upper casing and a periphery of the lower casing.

3. The cylinder pump of claim 1, wherein, in a central portion of the upper casing, is formed:
- a through hole through which passes:
  - an outer driving gear of the driving device, and
  - an inner driving gear positioned in the hollow of the outer driving gear, and, in the central portion of the upper rotator, are concentrically formed, in overlap:
- an outer driving gear joint hole that is joinable with the outer driving gear, and
- an inner driving gear through hole through which the inner driving gear can pass, and, in the central portion of the lower rotator, is formed:
- an inner driving gear joint hole joinable with the inner driving gear.

4. The cylinder pump of claim 1, wherein a flow rate of the liquid medication discharged through the outlet tube is determined by a cross sectional area of the cylinder and a rotation velocity of one of the first and second plungers driven by the driving device.

5. The cylinder pump of claim 1, wherein the driving device comprises:
- a first driving unit which, with the first plunger positioned between the inlet tube and the outlet tube, rotates with the second plunger in contact with a first side of the first plunger to come into contact with a second side of one the first plunger, so as to position the first plunger between the inlet tube and the outlet tube while shifting the first plunger; and
- a second driving unit which, with the second plunger positioned between the inlet tube and the outlet tube, rotates with the first plunger in contact with the first side of the first plunger to come into contact with the second plunger, so as to position the second plunger between the inlet tube and the outlet tube while shifting the second plunger, and the first driving unit and the second driving unit operate by taking turns.

6. The cylinder pump of claim 5, wherein the first driving unit and the second driving unit comprise:
- position retainers installed thereon so as to suppress arbitrary rotation of the first and second plungers.

7. The cylinder pump of claim 1, wherein, on an outer contour, where the upper casing and the lower casing face each other, are formed:
- an upper contour closing seat; and
- a lower contour closing seat, wherein a contour closer is sandwiched between the upper contour closing seat and the lower contour closing seat.

8. The cylinder pump of claim 7, wherein the upper contour closing seat and the lower contour closing seat protrude toward each other.

9. The cylinder pump of claim 1, wherein the driving device comprises:
- a housing which forms a body and has a mounting portion on one side of which the cylinder pump is detachably mounted;
- a driving motor installed in a first bracket fixed on the inside of the housing;
- a main driving shaft which is rotatably fixed to the first bracket, and is connected to an output shaft of the driving motor to rotate, wherein the main driving shaft is provided with an inner motor-driven gear and an outer motor-driven gear mounted thereon;
- an inner driving shaft which is rotatably fixed to the a second bracket fixed inside of the housing, wherein the inner driving shaft is provided with an inner driven gear meshed with the inner motor-driven gear, and an inner driving gear formed at an end of a journal portion thereof to engage with the upper rotator; and
- an outer driving shaft which has a boss portion into which the journal portion of the inner driving shaft is inserted, and is rotatably fixed to a second bracket, wherein the outer driving shaft is provided with an outer driven gear mounted thereon corresponding to the inner motor-driven gear meshed with the outer motor-driven gear, and an outer driving gear formed at an end of the boss portion to engage with the lower rotator, the inner driving gear and the outer driving gear are exposed through the mounting portion, the inner motor-driven gear and the outer motor-driven gear are identically formed gears, have gear teeth formed only on a part of each respective outer circumference, and the inner motor-driven gear and the outer motor-driven gear are placed in such a way that they have a phase difference of 180° with respect to the main driving shaft.

10. The cylinder pump of claim 9, wherein the inner motor-driven gear and the outer motor-driven gear have gear teeth formed only on a part of each respective outer circumference so that while rotating the inner driven gear and the outer driven gear $(360-\theta)°$, the inner driven gear and the outer driven gear can be rotated $(360-2X\theta)°$ only at a ½ rotation thereof.

11. The cylinder pump of claim 9, further comprising:
- an inner position retainer; and
- an outer position retainer which are installed in the second bracket for maintaining the position of the inner driven gear and the outer driven gear, in a state that the inner driven gear and the outer driven gear are not meshed with the inner motor-driven gear and the outer motor-driven gear, respectively.

12. The cylinder pump of claim 11, wherein each of the inner position retainer and the outer position retainer is provided with an inner boss seat and an outer boss seat having an M-shaped cross section for mounting an inner driven gear boss and an outer driven gear formed on respective surfaces of the inner driven gear and the outer driven gear.

* * * * *